(12) United States Patent
Chen et al.

(10) Patent No.: US 10,603,063 B2
(45) Date of Patent: Mar. 31, 2020

(54) SUTURING AND CUTTING APPARATUS FOR ENDOSCOPIC SURGERY

(71) Applicant: Suzhou Touchstone International Medical Science Co., Ltd., Suzhou (CN)

(72) Inventors: Wangdong Chen, Suzhou (CN); Tuo Shu, Suzhou (CN); Yanping Ye, Suzhou (CN)

(73) Assignee: SUZHOU TOUCHSTONE INTERNATIONAL MEDICAL SCIENCE CO., LTD., Suzhou (CN)

( * ) Notice: Subject to any disclaimer, the term of this patent is extended or adjusted under 35 U.S.C. 154(b) by 155 days.

(21) Appl. No.: 15/541,094

(22) PCT Filed: Dec. 30, 2015

(86) PCT No.: PCT/CN2015/099932
§ 371 (c)(1),
(2) Date: Jun. 30, 2017

(87) PCT Pub. No.: WO2016/107584
PCT Pub. Date: Jul. 7, 2016

(65) Prior Publication Data
US 2018/0132878 A1    May 17, 2018

(30) Foreign Application Priority Data

Dec. 30, 2014   (CN) .......................... 2014 1 0843677
Dec. 30, 2014   (CN) ..................... 2014 2 0859250 U

(51) Int. Cl.
*A61B 17/32*    (2006.01)
*A61B 17/068*   (2006.01)
(Continued)

(52) U.S. Cl.
CPC ...... *A61B 17/32002* (2013.01); *A61B 1/0008* (2013.01); *A61B 17/0469* (2013.01);
(Continued)

(58) Field of Classification Search
None
See application file for complete search history.

(56) References Cited

U.S. PATENT DOCUMENTS 10,226,249 B2 *   3/2019   Jaworek ........... A61B 17/07207
2002/0120252 A1   8/2002   Brock et al.
(Continued)

FOREIGN PATENT DOCUMENTS

CN    1843302 A      10/2006
CN    102440813 A    5/2012
(Continued)

OTHER PUBLICATIONS

European Search Report corresponding to European Application No. 15875260.0 dated Nov. 16, 2017.

*Primary Examiner* — Thomas Mcevoy
(74) *Attorney, Agent, or Firm* — Dickinson Wright PLLC

(57) ABSTRACT

A suturing and cutting apparatus for endoscopic surgery includes a body, a head portion, and a transmission mechanism, the head portion, is connected rotatably to a distal end of the body relative to the axial direction of the body by the transmission mechanism. The transmission mechanism includes an operating rod, a connecting assembly and a gear transmission mechanism. The connecting assembly includes a first conversion component which is set between the body and the head portion and can rotate relative to the axial direction of the body. The aspects disclosed herein allow and facilitate in the performance of the endoscopic surgery.

15 Claims, 7 Drawing Sheets

(51) Int. Cl.
*A61B 17/072* (2006.01)
*A61B 1/00* (2006.01)
*A61B 17/04* (2006.01)
A61B 17/29 (2006.01)
A61B 17/00 (2006.01)
A61B 17/06 (2006.01)

(52) U.S. Cl.
CPC ...... *A61B 17/068* (2013.01); *A61B 17/07207* (2013.01); *A61B 17/06066* (2013.01); *A61B 2017/00473* (2013.01); *A61B 2017/2927* (2013.01); *A61B 2017/2929* (2013.01)

(56) References Cited

U.S. PATENT DOCUMENTS

2011/0290855 A1   12/2011  Moore et al.
2013/0126586 A1*  5/2013   Zhang et al. .............. 227/176.1

FOREIGN PATENT DOCUMENTS

| CN | 102614006 A | 8/2012 |
| CN | 104207811 A | 12/2014 |
| CN | 204364047 U | 6/2015 |
| EP | 0795298 B1 | 9/1997 |
| EP | 1693018 A1 | 8/2006 |
| EP | 2371299 A1 | 10/2011 |
| EP | 2412319 A2 | 2/2012 |
| EP | 2415403 A1 | 2/2012 |
| EP | 2893882 A2 | 7/2015 |
| WO | 9518572 A1 | 7/1995 |

\* cited by examiner

SUTURING AND CUTTING APPARATUS FOR ENDOSCOPIC SURGERY

CROSS-REFERENCE TO RELATED APPLICATIONS

This application is a 371 national phase entry of PCT/CN2015/099932, filed 30 Dec. 2015, which claims the benefit of Chinese Patent Application No. 201410843677.1, filed 30 Dec. 2014, and Chinese Patent Application No. 201420859250.6 filed 30 Dec. 2014, the contents of which are incorporated herein by reference for all purposes.

TECHNICAL FIELD

The invention belongs to the field of medical instruments, relates to an operating instrument, more particularly, to a suturing and cutting apparatus for endoscopic surgery with a head portion capable of rotating.

BACKGROUND

A suturing and cutting apparatus for surgery has been widely used for suturing wounds, suturing and cutting internal tissues, and a suturing and cutting apparatus for endoscopic surgery has been exploited nowadays. Endoscopic surgery, also called laparoscope surgery, uses electron images instead of looking with naked eyes, uses a slender instrument instead of fingers, and aims to accomplish observation, diagnosis, cutting, suturing and other therapies with a smallest incision path, a minimum damage of tissues, a least stress reaction of organisms.

The suturing and cutting apparatus for endoscopic surgery, generally comprises an instrument platform and a head portion mounted detachably on this platform, the instrument platform comprises an actuating handle, the detachable head portion comprises a body and a head portion mounted on the distal end of the body, the body comprises a sleeve and an actuating assembly set in the sleeve; the head portion is a portion to implement the action of cutting and suturing, which comprises a cartridge assembly, an anvil assembly and a cutting assembly, the head portion of the suturing and cutting apparatus can get close to the operating position with a trocar going through a little incision of body to operate. Under the actuation of the actuating handle, the actuating assembly pushes the cartridge assembly and the cutting assembly to accomplish the suturing and cutting operation. Generally, the head portion is mounted on the distal end of the body with an articulated mechanism, with this articulated mechanism, users can remotely operate the head portion to make it to rotate clockwise or anticlockwise relative to the body.

In the suturing and cutting apparatus for endoscopic surgery nowadays, the head portion can be rotated to any side relative to the body at a largest angle of about 45 degree, which usually cannot fulfill the operating requirement of a surgery doctor in specific operation practices. Hence, nowadays, there is an urgent need for a suturing and cutting apparatus for endoscopic surgery with a head portion capable of being rotated a larger angle.

SUMMARY

The purpose of the invention is to provide a suturing and cutting apparatus for endoscopic surgery with a head portion capable of being rotated a larger angle.

The invention provides a suturing and cutting apparatus for endoscopic surgery, comprising: a body, a head portion, and a transmission mechanism, said head portion is connected rotatably to a distal end of said body relative to the axial direction of said body by means of said transmission mechanism; wherein, said transmission mechanism comprises: an operating rod, a connecting assembly and a gear transmission assembly, said connecting assembly comprises a first conversion component, a proximal end of said first conversion component is connected rotatably to said body, a distal end of said first conversion component is connected rotatably to said head portion; said operating rod has an actuation end and a linkage end; the linkage end of said operating rod is connected to said first conversion component; when the actuation end of said operating rod is subjected to an action force, said first conversion component is rotated relative to the axial direction of said body by the linkage end of said operating rod, and said head portion is rotated in the same direction relative to said first conversion component by means of the transmission of said transmission assembly.

In a preferable embodiment of the invention, the linkage end of said operating rod is articulated with said first conversion component by a first articulated portion; said connecting assembly further comprises a first connecting component and a second connecting component; said first connecting component is fixed to said body; the proximal end of said first conversion component is articulated with said first connecting component by a second articulated portion, the distal end of said first conversion component is fixed to said second connecting component; said second connecting component is articulated with said head portion by a third articulated portion.

In a preferable embodiment of the invention, an input end of said gear transmission assembly is fixed relative to said first connecting component, an output end of said gear transmission assembly is fixed relative to said head portion, the rotating direction of the output end of said gear transmission assembly relative to said third articulated portion is the same with the rotating direction of said first conversion component relative to said second articulated portion.

In a preferable embodiment of the invention, the input end of said gear transmission assembly is a first tooth portion fixed to said body or to a distal end of said first connecting component; the output end of said gear transmission assembly is a second tooth portion fixed to a proximal end of said head portion.

In a preferable embodiment of the invention, said first tooth portion is formed directly on the distal end of said first connecting component.

In a preferable embodiment of the invention, the distal end of said first connecting component is fixed to a fixed-axle gear, a distal end of said fixed-axle gear forms said first tooth portion.

In a preferable embodiment of the invention, there is a limiting component fixed on the distal end of said first connecting component, said limiting component engages with the tooth portion at a proximal end of said fixed-axle gear, or clamps and cooperates with at least one tooth groove at the proximal end of said fixed-axle gear.

In a preferable embodiment of the invention, said fixed-axle gear is set to sheathe the articulated shaft of said second articulated portion, and is set between said first connecting component and said first conversion component.

In a preferable embodiment of the invention, said second tooth portion is formed directly at an end face on a proximal end of said head portion.

In a preferable embodiment of the invention, said gear transmission assembly is a parallel-axle gear transmission assembly set along the axial direction of the body.

In a preferable embodiment of the invention, said gear transmission assembly is a cylindrical spur gear transmission assembly.

In a preferable embodiment of the invention, said gear transmission assembly comprises a drive gear and a driven gear set; the mandrels of said drive gear and driven gear set are both fixed to said first conversion component; a proximal end of said drive gear engages with said input end, a distal end thereof engages with a proximal end of said driven gear set; one end of a distal end of said driven gear set engages with said output end; said driven gear set comprises a driven gear or more than one driven gears engaging with each other in turn, and the number of the driven gears is odd number.

In a preferable embodiment of the invention, the axial centers of said second articulated portion, said drive gear, said driven gear set and said third articulated portion are all on a same straight line.

In a preferable embodiment of the invention, said first conversion component and said second connecting component are fixed with each other by a fixed axle; at least one driven gear of said driven gear set is set to sheathe said fixed axle, and the driven gear is set between said second connecting component and said first conversion component.

In a preferable embodiment of the invention, there is an opening at a distal end of the sleeve of said body, when the linkage end of said operating rod is moved to said opening, said linkage end and said first articulated portion come out of said opening.

In the suturing and cutting apparatus for endoscopic surgery, the first conversion component which can be rotated relative to the axial direction of the body is added between the body and the head portion, with the transmission of the connecting assembly and the gear transmission assembly, while the head portion rotates in the same direction relative to the axial direction of the body along with the first conversion component, the rotation of the first conversion component is transmitted to the head portion by the gear transmission assembly, so the head portion further rotates in the same direction relative to the first conversion component, so the head portion can rotate a larger angle relative to the body, and the requirement of endoscopic surgery can be better fulfilled.

DETAILED DESCRIPTION

Hereinafter, the invention is described in detail with reference to the embodiments shown in the accompanying figures. But the embodiments are not a limitation to the invention, and the conversions of structure, method or function made by the ordinary technicians in the art according to the embodiments are all included in the protection scope of the invention.

The expressions of position and direction in the invention, all refer to the operator of the instrument, the proximal end is the end close to the operator, and the distal end is the end far from the operator. The axial direction means the direction of length from the distal end to the proximal end.

"First", "second" and so on mentioned in the embodiment don't comprise an absolute divisive relationship of position relationship or structural function, and, in different embodiments, same marks or reference numbers may be used only for a convenient description, which also don't mean the relationship of structure or function.

According to FIG. 1 to FIG. 7, a specific embodiment of the suturing and cutting apparatus for endoscopic surgery of the invention is introduced.

Figure 1:
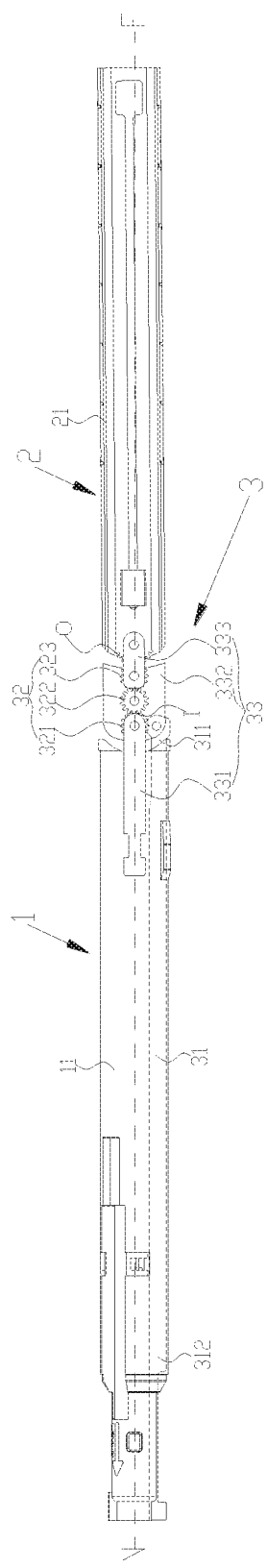
FIG. 1 is a top schematic view of the suturing and cutting apparatus for endoscopic surgery in a first status according to a specific embodiment of the invention.
Figure 2:
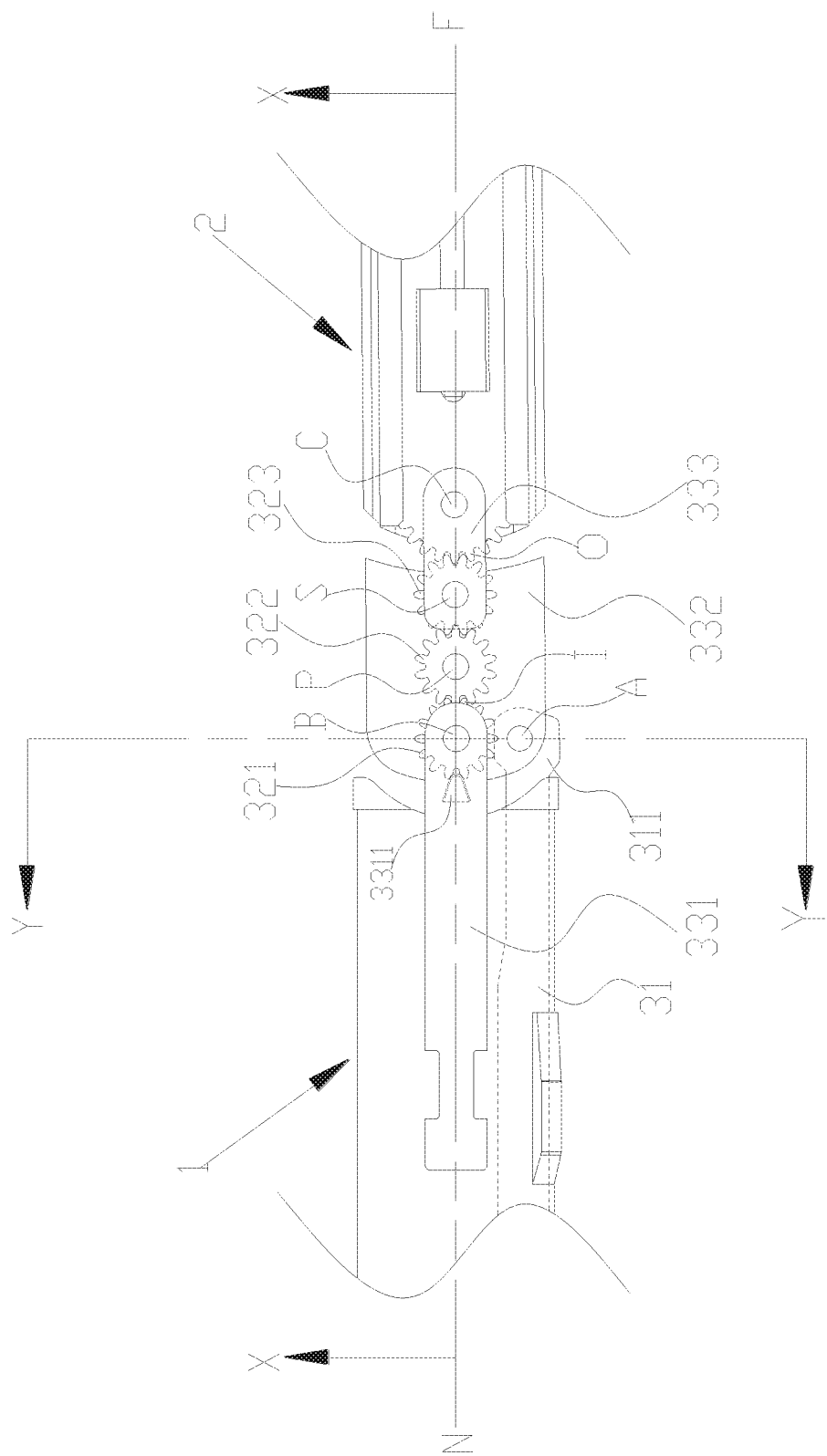
FIG. 2 is a top schematic view of the suturing and cutting apparatus for endoscopic surgery in a first status according to a specific embodiment of the invention.
Figure 3:
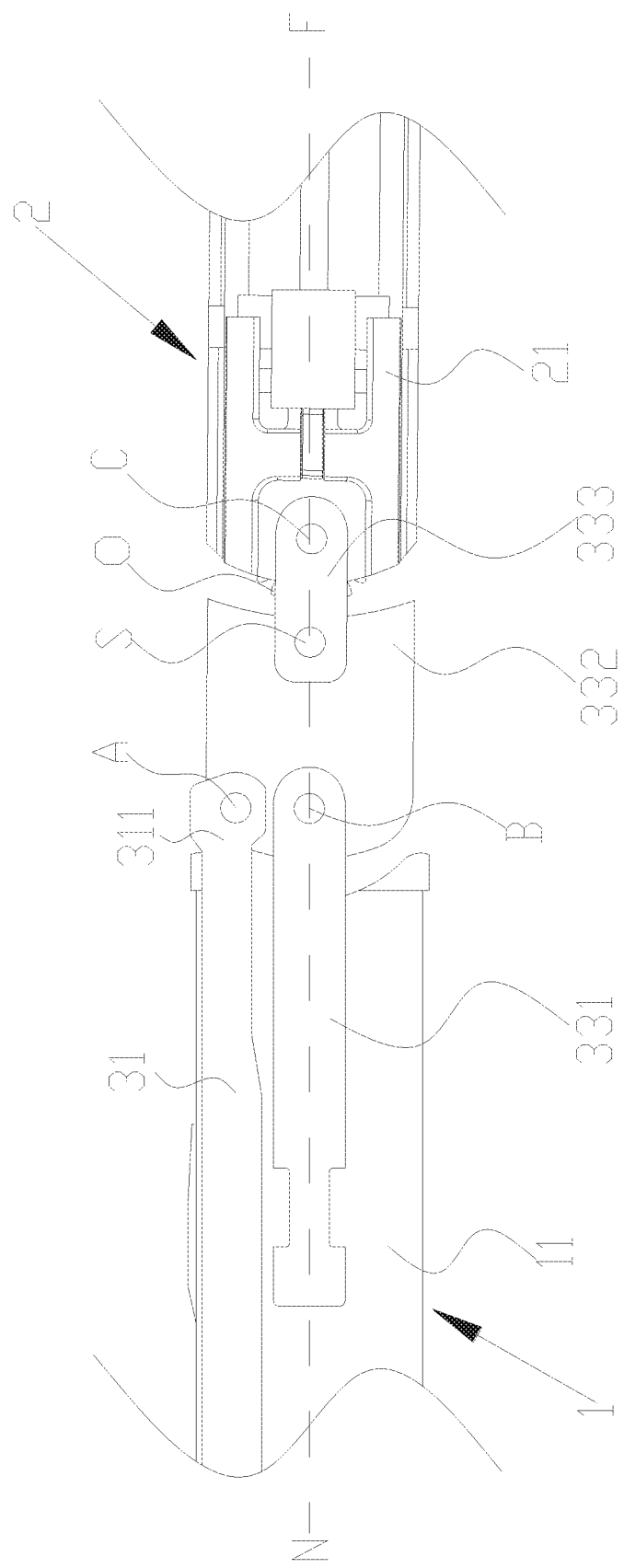
FIG. 3 is a bottom schematic view of the suturing and cutting apparatus for endoscopic surgery in a first status according to a specific embodiment of the invention.

According to FIG. 1 to FIG. 3, the apparatus comprises: a body 1, a head portion 2 and a transmission mechanism 3, the head portion 2 is connected to a distal end of the body 1 rotatably relative to the axial direction of the body 1 by means of the transmission mechanism 3.

In the embodiment, the body 1 comprises a sleeve 11 and an actuating assembly set in the sleeve 11 and so on (not shown in the figures).

In the embodiment, the head portion 2 is a portion to the action of cutting and suturing, the head portion 2 can comprises a cartridge assembly, an anvil assembly, a cutting assembly and so on, the figures only show the cartridge support 21 set along the axial direction of the head portion 2.

The transmission mechanism 3 comprises: an operating rod 31, a gear transmission assembly 32 and a connecting assembly 33.

The connecting assembly 33 at least comprises a first conversion component 332, a proximal end of the first conversion component 332 is connected rotatably to the body 1, and a distal end of the first conversion component 332 is connected rotatably to the head portion 2.

The operating rod 31 has an actuation end 312 and a linkage end 311. The linkage end 311 of the operating rod 31 is connected to the first conversion component 332. In the embodiment, the operating rod 31 is articulated with the first conversion portion 332 by a first articulated portion A. Specifically, in the embodiment, there is a cylindrical pin fixed on the first conversion component 332 as the first articulated portion A, and there is a pin groove set at the linkage end 311 to cooperate with the cylindrical pin. In an alternative embodiment of the invention, there can be a cylindrical pin fixed on the linkage end 311 as the first articulated portion A, and there is a pin groove set on the first conversion component 332 to cooperate with the cylindrical pin; other ways of pivot connecting/articulating can also be adopted.

In the embodiment, the linkage end 311 is set slidably in the body 1. In the embodiment, the linkage end 311 slides generally along the sleeve 11 to the distal end or the proximal end.

In the embodiment, the connecting assembly 33 further comprises a first connecting component 331 and a second connecting component 333. The first connecting component 331 is fixed to the body 1. The proximal end of the first conversion component 332 is articulated with the first connecting component 331 by a second articulated portion B. The distal end of the first conversion component 332 is fixed to a proximal end of the second connecting component 333. A distal end of the second connecting component 333 is articulated with the head portion 2 by a third articulated portion C.

In the embodiment, the first conversion component 332 and the second connecting component 333 are fixed with each other by a fixed axle S, wherein the fixed axle S can be a cylinder axle fixed on the second connecting component 333, or can be a cylinder axle fixed on the first conversion component 332.

Apply an action force at the actuation end 312 of the operating rod 31, the linkage end 311 is moved, so the first conversion component 332 is rotated relative to the axial direction of the body 1 around the second articulated portion B, with the transmission of the second connecting component 333, the head portion 2 is rotated at a first angle in the same direction relative to the axial direction of the body 1 along with the first conversion component 332; meanwhile, the rotation of the first conversion component 332 around the second articulated portion B is transmitted to the head portion 2 by the gear transmission assembly 32, so the head portion 2 rotates a second angle in the same direction relative to the first conversion component 332 around the third articulated portion C. Finally, the rotation angle of the head portion 2 relative to the axial direction of the body 1 is a sum of the first angle and the second angle.

In an alternative embodiment of the invention, the linkage end 311 of the operating rod 31 is connected rotatably or fixedly in other ways to the first conversion component 332, as long as the first conversion component 332 can be driven by the linkage end 311 of the operating rod 31, then the first conversion component 332 can be rotated relative to the axial direction of the body 1.

In an alternative embodiment of the invention, the first connecting component 331 can be articulated with the body 1; the proximal end of the first conversion component 332 is fixed to the first connecting component 331. Other embodiments can also be adopted, as long as the rotation of the first conversion component 332 relative to the axial direction of the body 1 can be realized.

In an alternative embodiment of the invention, the distal end of the first conversion component 332 is articulated with the proximal end of the second connecting component 333, and the distal end of the second connecting component 333 is fixed to the head portion 2. Other embodiments can also be adopted, as long as the rotation of the head portion 2 relative to the first conversion component 332 can be realized.

An input end of the gear transmission assembly 32 is fixed relative to the first connecting component 331, an output end of the gear transmission assembly 32 is fixed to the head portion 2; the rotating direction of the output end of the gear transmission assembly 32 relative to the third articulated portion C is the same with the rotating direction of the first conversion component 332 relative to the second articulated portion B.

The input end of the gear transmission assembly 32 is a first tooth portion I fixed to the body 1 or to the distal end of the first connecting component 331. Specifically, the first tooth portion I can be formed directly on the distal end of the first connecting component 331; or set fixedly on the distal end of the first connecting component 331 as an independent component.

In the embodiment of the invention, there is an independent component fixed on the distal end of the first connecting component 331, that is, a fixed-axle gear 321, the tooth portion at a distal end of the fixed-axle gear 321 is the first gear portion I. The fixed connecting method of the first connecting component 331 and the fixed-axle gear 321 can be referred in FIG. 2, FIG. 4 and FIG. 5, in the embodiment, there is a limiting component 3311 fixed inside the distal end of the first connecting component 331 and close to a proximal end of the fixed-axle gear 321, the limiting component 3311 clamps and cooperates with at least one tooth groove at the proximal end of the fixed-axle gear 321. The limiting component 3311 can be a bump clamping and cooperating with the tooth groove. In an alternative embodiment of the invention, the limiting component 3311 engages with the tooth portion on the proximal end of the fixed-axle gear 321.

Figure 4:
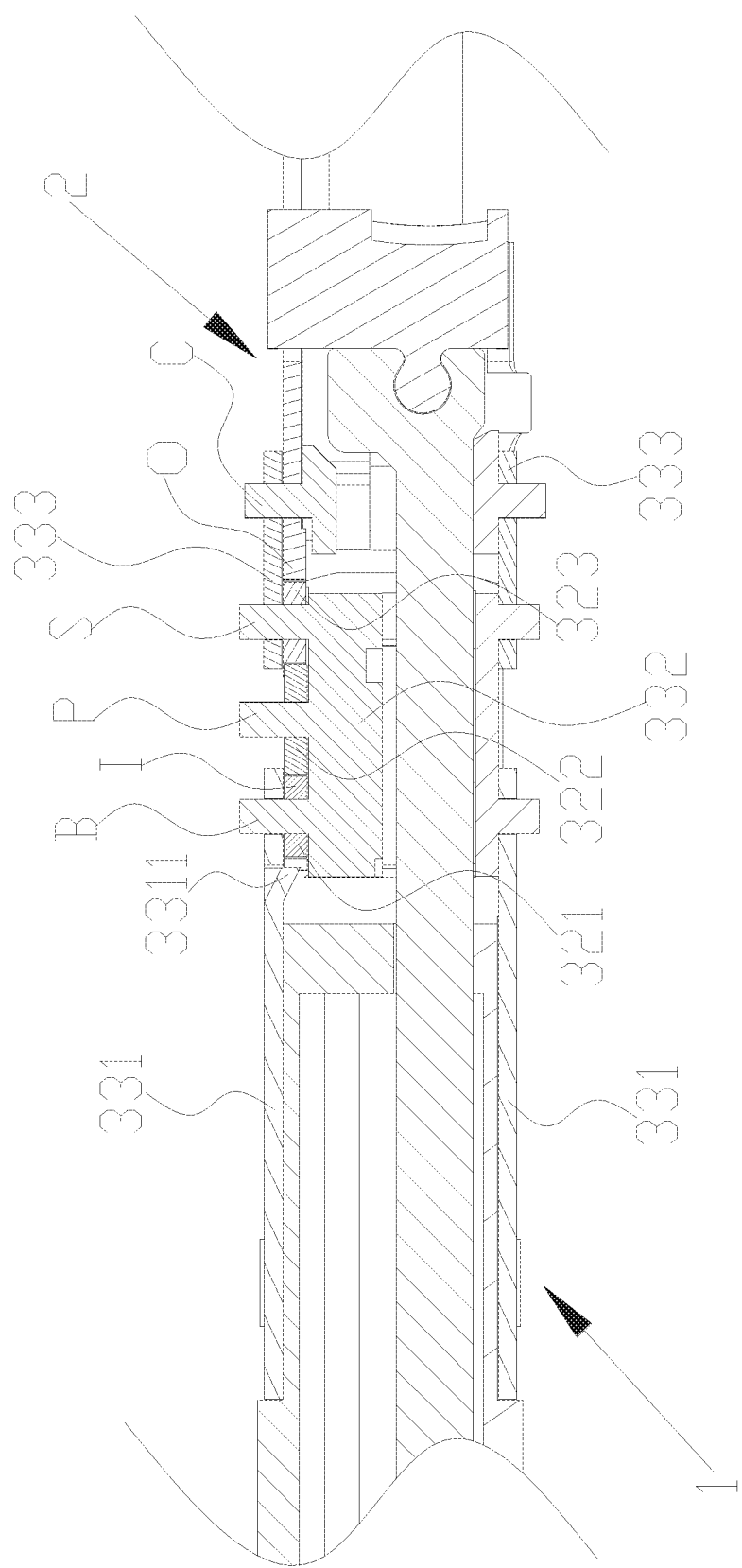
FIG. 4 is a section schematic view of FIG. 2 in X-X direction.
Figure 5:
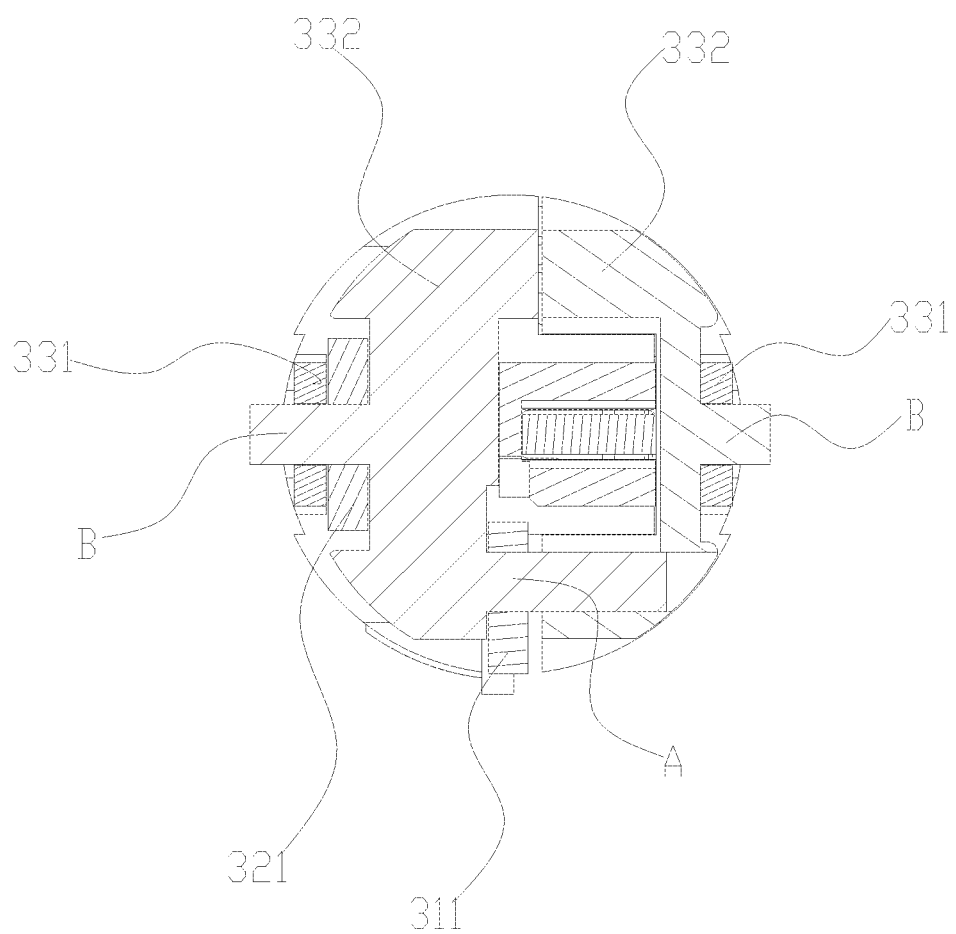
FIG. 5 is a section schematic view of FIG. 2 in Y-Y direction.

In the embodiment, as shown in FIG. 4 and FIG. 5, the fixed-axle gear 321 is set to sheathe the articulated shaft of the second articulated portion B, and is set between the first connecting component 331 and the first conversion component 332, so that the structure is compact.

In an alternative embodiment of the invention, the first tooth portion I can be formed directly at the end face of the distal end of the first connecting component 331, the first tooth portion I can also be formed directly on the first articulated portion B, the first tooth portion I fixed to the body 1 and the first connecting component 331 can also be formed in other methods.

The output end of the gear transmission assembly 32 is a second tooth portion O fixed on a proximal end of the head portion 2. In the embodiment of the invention, the second tooth portion O is formed directly at the end face of a proximal end of the head portion 2, such as formed directly at the end face of a proximal end of the cartridge support 21. In an alternative embodiment, a second fixed-axle gear can also be fixed on the proximal end of the cartridge support 21, and the tooth portion at the proximal end of the fixed-axle gear is the second tooth portion O. The second fixed-axle gear can be set at the place of the third articulated portion C (that is, the mandrel of the second fixed-axle gear is coincide with the articulated shaft of the third articulated portion C, the second fixed-axle gear is set to sheathe the articulated shaft of the third articulated portion C, and rotates around the articulated shaft). The fixed connecting method between the second-axle gear and the head assembly 2 can be similar with the fixed-axle gear 321 above, which will not be repeated here.

In the embodiment of the invention, the gear transmission assembly 32 is a parallel-axle gear transmission assembly set along the axial direction of the body 1, and the parallel-axle gear transmission assembly is a cylindrical spur gear transmission assembly. The axial center of each gear of the parallel-axle gear transmission assembly can be set to a line along the axial direction of the body 1 (as shown in FIG. 1), and can also be set to other shapes, such as triangle, sawtooth and so on. The specific arrangement method and the shape of the tooth are not limited by this, such as the gear axles can be intersected or staggered with each other, and the tooth shape can be straight tooth, helical tooth, herringbone tooth and so on.

The gear transmission assembly 32 comprises a drive gear 322 and a driven gear 323. The mandrels of the drive gear 322 and driven gear 323 are both fixed relative to the first conversion component 332. A proximal end of the drive gear 322 engages with the first tooth portion I on the input end, a distal end engages with a proximal end of the driven gear 323; the distal end of the driven gear 323 engages with the second tooth portion O on the output end.

In the embodiment, the mandrel of the drive gear 322 is fixed on the first conversion component 332, specifically, the drive gear 322 is set to rotatably sheathe the fixed axle P of the first conversion component 332.

In the embodiment, the first conversion component 332 is fixed to the second connecting component 333 by a fixed axle S. As shown in FIG. 4, the driven gear 323 is set to rotatably sheathe the fixed axle S, and the driven gear 323 is set between the second connecting component 333 and the first conversion component 332, so that the structure is compact.

In the embodiment, the first connecting component 331 has two halves set generally symmetric with each other, and the center axis of the body 1 is the axis of symmetry. One half is set above (the first connecting component 331 shown in the top views of FIG. 1 and FIG. 2), the other half is set under (the first connecting component 331 shown in the bottom view of FIG. 3), the two halves of the first connecting component 331 are all marked as 331 in the figures, which can be seen in FIG. 4 and FIG. 5. Similarly, both the second connecting component 333 and the first conversion component 332 have two halves generally symmetric with each other, and they are all marked uniformly as 333, 332 in the figures, as long as the gear transmission assembly 32 is connected with the parts of the first connecting component 331, the first conversion component 332 and the second connecting component 333 set on a same side.

In an alternative embodiment, the gear transmission assembly 32 comprises a drive gear 322 and a driven gear set, the driven gear set comprises more than one driven gears engage with each other in turn and the number of the driven gears is odd number. The proximal end of the drive gear set engages with the drive gear 322, the distal end engages with the second tooth portion O.

In the embodiment, the second articulated portion B, axial center of the drive gear 322, the axial center of the drive gear 323 and the axial center of the third articulated portion C are all in a same line.

In the embodiment, the axial center of the second articulated portion B is set on the central axial line of the body 1; the axial center of the third articulated portion C is set on the central axial line of the head portion 2; the line between the axial centers of the second articulated portion B and the third articulated portion C is in a same line with the central axial line of the first conversion component 332.

Below combining with FIG. 2, FIG. 3, FIG. 6 and FIG. 7, it is illustrated that how the suturing and cutting apparatus for endoscopic surgery of the embodiment of the invention realizes that the head portion 2 and the first conversion component 332 rotate in a same direction relative to the axial direction of the body 1.

As shown in FIG. 2 and FIG. 3, it's a first status of the apparatus. The head portion 2 and the first conversion component 332 don't rotate relative to the body 1. In the embodiment, in the first status, the body 1, the first conversion component 332 and the head portion 2 are set generally coaxially, that is, the central axial lines of the body 1, the first conversion component 332 and the head portion 2 are generally on a same straight line; besides, the second articulated portion B, the axial center of the drive gear 322, the axial center of the driven gear 323 and the axial center of the third articulated portion C are also set on this straight line.

Figure 6:
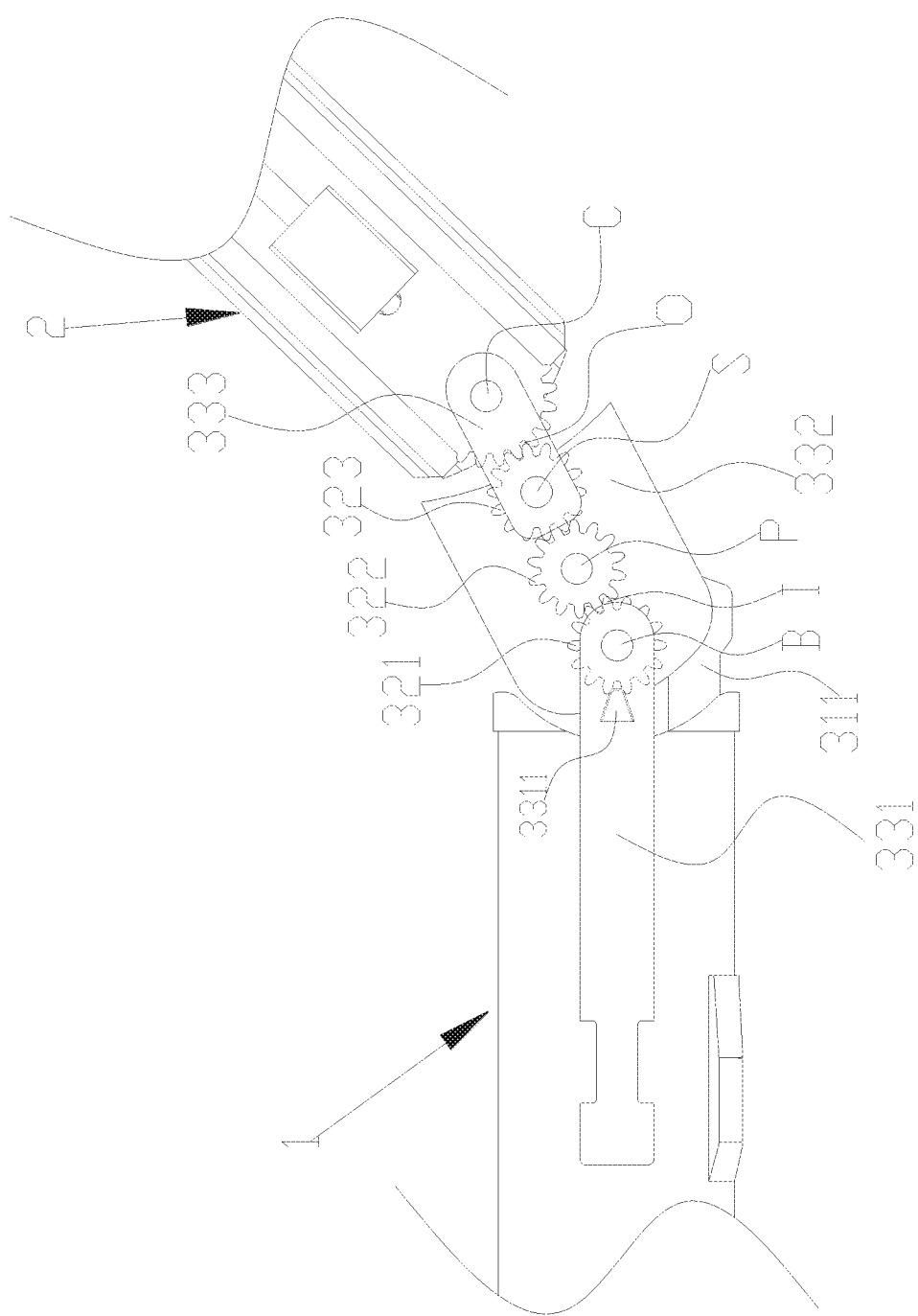
FIG. 6 is a top schematic of the suturing and cutting apparatus for endoscopic surgery in a second status according to a specific embodiment of the invention.

As shown in FIG. 6, it's a second status of the apparatus. When the operator operates the actuating end 312 of the operating rod 31 to apply a pushing force towards the distal end, the linkage end 311 slides along the sleeve 11 of the body 1 towards to the distal end; the linkage end 311 applies a force towards the distal end to the first conversion component 332 at the place of the first articulated portion A, then the first conversion component 332 rotates anticlockwise relative to the axial direction of the body 1 around the second articulated portion B; meanwhile, with the transmission of the second connecting component 333, along with the second connecting component 333 and the first conversion component 332, the head portion 2 also rotates anticlockwise relative to the axial direction of the body 1 around the second articulated portion B; meanwhile, the anticlockwise rotation of the first conversion component 332 relative to the axial direction of the body 1 around the second articulated portion B is transmitted to the head portion 2 by the gear transmission assembly 32, then the head portion 2 further rotates anticlockwise relative to the first conversion component 332 around the third articulated portion C, so the head portion 2 can rotate anticlockwise at a larger angle relative to the axial direction of the body 1.

As to the transmission process of the gear transmission assembly 32, details are as follows: for the fixed-axle gear 321 is fixed to the first connecting component 321, so the first tooth portion I on the distal end of the fixed-axle gear 321 stops rotating relative to the axial center of the second articulated portion B; when the mandrel of the drive gear 322 and the mandrel of the driven gear 323 both rotate together around the second articulated portion B along with the first conversion component 332, the first tooth portion I is against the tooth portion at a proximal end of the drive gear 322, so that the drive gear 322 is rotated anticlockwise around its own mandrel, the drive gear 322 leads the driven gear 323 to rotate clockwise around its own mandrel, the rotation of the driven gear 323 is outputted to the second gear portion O of the head portion 2, so the head portion 2 further rotates anticlockwise relative to the first conversion component 332 around the third articulated portion C.

Figure 7:
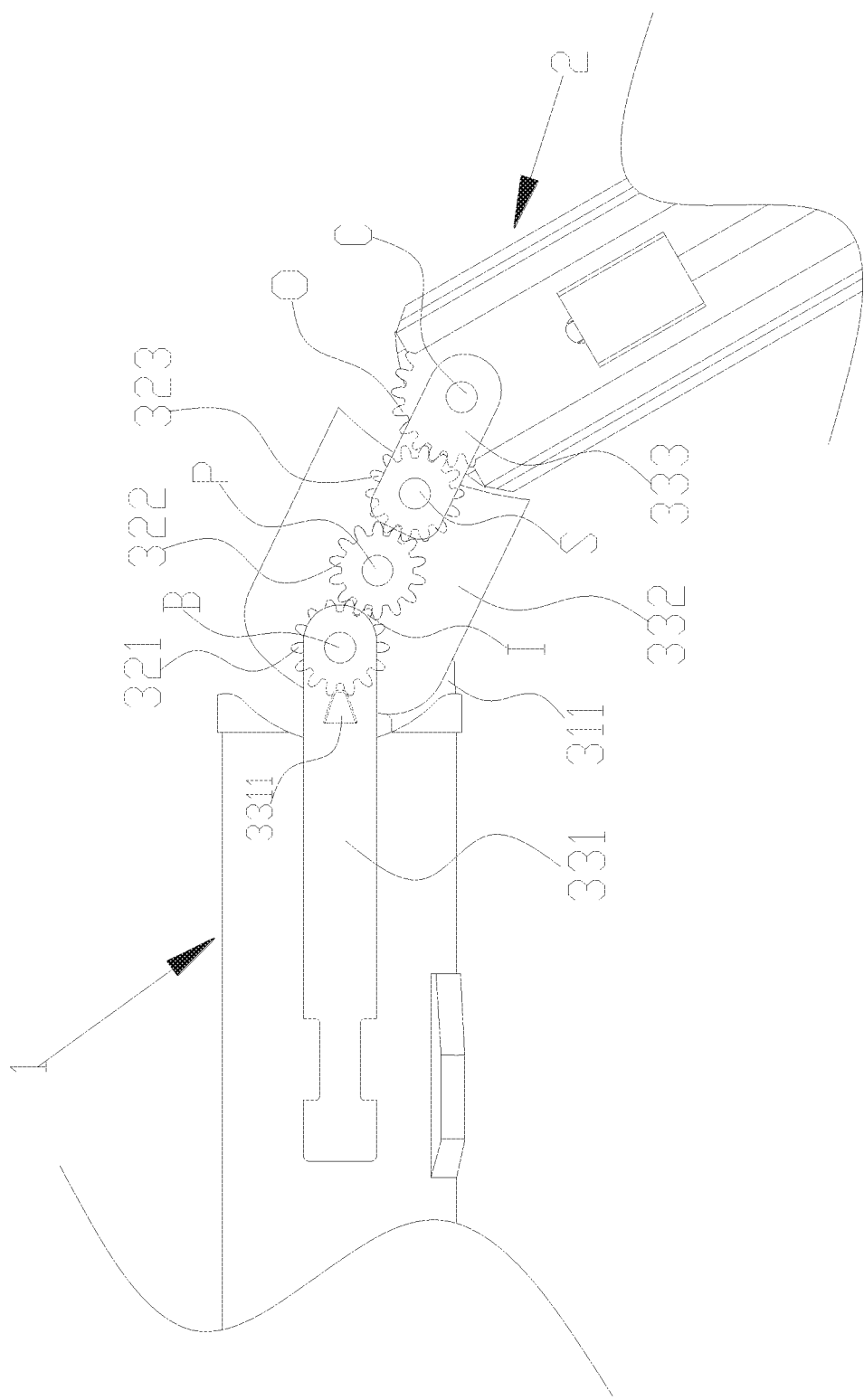
FIG. 7 is a top schematic of the suturing and cutting apparatus for endoscopic surgery in a third status according to a specific embodiment of the invention.

As shown in FIG. 7, it's a third status of the apparatus. When the operator operates the actuating end 312 of the operating rod 31 to apply a pulling force towards the proximal end, the linkage end 311 slides along the sleeve 11 of the body 1 towards the proximal end; the linkage end 311 applies a force towards the proximal end to the first conversion component 332 at the place of the first articulated portion A, then the first conversion component 332 rotates clockwise relative to the axial direction of the body 1 around the second articulated portion B; meanwhile, with the transmission of the second connecting component 333, along with the second connecting component 333 and the first conversion component 332, the head portion 2 also rotates clockwise relative to the axial direction of the body 1 around the second articulated portion B; meanwhile, the clockwise rotation of the first conversion component 332 relative to the axial direction of the body 1 around the second articulated portion B is transmitted to the head portion 2 by the gear transmission assembly 32, then the head portion 2 further rotates clockwise relative to the first conversion component 332 around the third articulated portion C, so the head portion 2 can rotate clockwise at a larger angle relative to the axial direction of the body 1.

As to the transmission process of the gear transmission assembly 32, it's opposite with the transmission process of the gear transmission assembly 32 shown in FIG. 6 illustrated above, and will not be repeated here.

As shown in FIG. 6 and FIG. 7, the first conversion component 332 rotates at a first angle to one side relative to the axial direction of the body 1, the head portion 2 further rotates at a second angle in the same direction relative to the first conversion component 332, so, the head portion 2 rotates a larger angle to one side relative to the axial direction of the body 1, that is, the sum of the first angle and the second angle. Generally, in the existing technology, the largest rotating angle of the head portion 2 to any side relative to the axial direction of the body 1 is around 45 degrees, but in the apparatus of the embodiment, the largest rotating angle of the head portion 2 to any side relative to the axial direction of the body 1 can reach 60 degrees, and a larger rotating angle can be gotten by adjusting the transmission ratio of the gears, and the requirements for endoscopic surgery can be better fulfilled.

In an alternative embodiment, the rotating angle of the head portion 2 relative to the first conversion component 332 can be larger than the rotating angle of the first conversion component 332 relative to the body 1, and the head portion 2 can have a larger degree of rotating freedom.

It should be understood that, although the specification is described according to the embodiments, but not each embodiment only comprises a single technical proposal, the description of the specification is only for clear, the technicians in the art should consider the specification as an entirety, the technical proposals of the embodiments can also be combined properly, to form other embodiments that the technicians in the art can understand.

The series of specific illustrations listed above are only specific illustrations aiming at the methods for feasibility embodiments, they are not used as a limitation to the protect scope of the invention, equivalent embodiments or alterations made without being apart from the art spirit of the invention should all be included in the protection scope of the invention.

What is claimed is:

1. A suturing and cutting apparatus for endoscopic surgery, comprising:
    a body, a head portion, and a transmission mechanism, said head portion connected rotatably to a distal end of said body relative to an axial direction of said body by said transmission mechanism;
    wherein,
    said transmission mechanism comprises: an operating rod, a connecting assembly and a gear transmission assembly,
    said connecting assembly comprises: a first conversion component, a proximal end of said first conversion component connected rotatably to said body, a distal end of said first conversion component connected rotatably to said head portion;
    said operating rod has an actuation end and a linkage end; the linkage end of said operating rod is connected to said first conversion component;
    in response to the actuation end of said operating rod being subjected to an action force, said first conversion component is rotated relative to the axial direction of said body by the linkage end of said operating rod, and said head portion is rotated in the same direction relative to said first conversion component by of the transmission of force by said transmission assembly, wherein the linkage end of said operating rod is articulated with said first conversion component by a first articulated portion located on said first conversion component.

2. The suturing and cutting apparatus for endoscopic surgery according to claim 1, wherein,
    said connecting assembly further comprises a first connecting component and a second connecting component;
    said first connecting component is fixed to said body; the proximal end of said first conversion component is articulated with said first connecting component by a second articulated portion, the distal end of said first conversion component is fixed to said second connecting component; said second connecting component is articulated with said head portion by a third articulated portion.

3. The suturing and cutting apparatus for endoscopic surgery according to claim 2, further comprising:
    an input end of said gear transmission assembly being fixed relative to said first connecting component,
    an output end of said gear transmission assembly being fixed relative to said head portion, the rotating direction of the output end of said gear transmission assembly relative to said third articulated portion is the same with the rotating direction of said first conversion component relative to said second articulated portion.

4. The suturing and cutting apparatus for endoscopic surgery according to claim 3, wherein,
    the input end of said gear transmission assembly is a first tooth portion fixed to said body or to a distal end of said first connecting component;
    the output end of said gear transmission assembly is a second tooth portion fixed to a proximal end of said head portion.

5. The suturing and cutting apparatus for endoscopic surgery according to claim 4, wherein, said first tooth portion is formed directly on the distal end of said first connecting component.

6. The suturing and cutting apparatus for endoscopic surgery according to claim 4, wherein, the distal end of said first connecting component is fixed to a fixed-axle gear, a distal end of said fixed-axle gear forms said first tooth portion.

7. The suturing and cutting apparatus for endoscopic surgery according to claim 6, further comprising a limiting component fixed on the distal end of said first connecting component, said limiting component engages with the tooth portion at a proximal end of said fixed-axle gear, and clamps and cooperates with at least one tooth groove at the proximal end of said fixed-axle gear.

8. The suturing and cutting apparatus for endoscopic surgery according to claim 6, wherein, said fixed-axle gear is set to sheathe an articulated shaft of said second articulated portion, and is set between said first connecting component and said first conversion component.

9. The suturing and cutting apparatus for endoscopic surgery according to claim 4, wherein, said second tooth portion is formed directly at an end face on a proximal end of said head portion.

10. The suturing and cutting apparatus for endoscopic surgery according to claim 9, wherein, said gear transmission assembly is a parallel-axle gear transmission assembly set along the axial direction of the body.

11. The suturing and cutting apparatus for endoscopic surgery according to claim 10, wherein, said gear transmission assembly is a cylindrical spur gear transmission assembly.

12. The suturing and cutting apparatus for endoscopic surgery according to claim 11, wherein,
said gear transmission assembly comprises a drive gear and a driven gear set;
a plurality of mandrels of said drive gear and driven gear set are both fixed to said first conversion component; a proximal end of said drive gear engages with said input end, a distal end thereof engages with a proximal end of said driven gear set; one end of a distal end of said driven gear set engages with said output end;
said driven gear set comprises a driven gear or more than one driven gears engaging with each other in turn, and the number of the driven gears is odd number.

13. The suturing and cutting apparatus for endoscopic surgery according to claim 12, wherein, the axial centers of said second articulated portion, said drive gear, said driven gear set and said third articulated portion are all on a same straight line.

14. The suturing and cutting apparatus for endoscopic surgery according to claim 12, wherein,
said first conversion component and said second connecting component are fixed with each other by a fixed axle;
at least one driven gear of said driven gear set is set to sheathe said fixed axle, and the driven gear is set between said second connecting component and said first conversion component.

15. The suturing and cutting apparatus for endoscopic surgery according to claim 1 further comprising, an opening at a distal end of a sleeve of said body, wherein in response to the linkage end of said operating rod being moved to said opening, said linkage end and said first articulated portion are provided to come out of said opening.

\* \* \* \* \*